United States Patent [19]

Becker et al.

[11] Patent Number: 5,604,108

[45] Date of Patent: Feb. 18, 1997

[54] TEST FOR DETERMINING THE DOSE RESPONSE OF A CONJUGATED VACCINE

[75] Inventors: Robert S. Becker, Henryville; Karen Biscardi, South Sterling; Patrick McVerry; Robert Ryall, both of Stroudsburg, all of Pa.

[73] Assignee: Connaught Laboratories, Inc., Swiftwater, Pa.

[21] Appl. No.: 253,251

[22] Filed: Jun. 2, 1994

Related U.S. Application Data

[63] Continuation of Ser. No. 943,171, Sep. 14, 1992, abandoned.

[51] Int. Cl.$^6$ .......................... G01N 33/554; A61K 49/00
[52] U.S. Cl. .......................... 435/7.32; 424/9.2; 424/256.1; 424/245.1; 424/197.11; 424/203.1; 424/234.1; 424/193.1
[58] Field of Search .......................... 435/7.32, 967; 424/193.1, 197.11, 203.1, 234.1, 256.1, 245.2, 9.2

[56] References Cited

U.S. PATENT DOCUMENTS 4,496,538  1/1985  Gordon .
4,619,828  10/1986  Gordon .
4,644,059  2/1987  Gordon .

OTHER PUBLICATIONS

Vella, P. P. et al. "Immunogenicity of a New *Haemophilus influenzae* type b Conjugate Vaccine" Pediatrics 85(4 part 2):668–74, 1990.

John. J. Donnelly et al. "Immunogenicity of A *Haemophilus influenzae* polysaccharide–*Neisseria meningitidis* outer membrane protein complex conjugate vaccine", Journal of Immunology 145:3071–9, 1990.

Juhani Eskola, et al. "Simultaneous administration of *Haemophilus influenzae* type b capsular polysaccharide–diphtheria tetanus–pertussis and inactivated poliovirus vaccinations of childhood". Pediatr. Infect. Dis. 7:480–4, 1988.

*Primary Examiner*—James C. Housel
*Assistant Examiner*—Jennifer Shaver
*Attorney, Agent, or Firm*—Curtis Morris & Safford P.C.

[57] ABSTRACT

The dosage response of humans to conjugate vaccines comprising a bacterial polysaccharide and a strongly-immunogenic carrier protein is determined in animals by coadministering to the animal unconjugated strongly-immunogenic carrier protein in an amount corresponding, on a weight-related basis, to that administered to the human.

2 Claims, 2 Drawing Sheets

TEST FOR DETERMINING THE DOSE RESPONSE OF A CONJUGATED VACCINE

This is a Rule 60 Continuation, of application Ser. No. 07/943,171, filed Sep. 14, 1992, now abandoned.

FIELD OF INVENTION

The present invention relates to the testing of vaccines and, in particular, to the mimicking the immune response to a vaccine in humans by testing in animals.

BACKGROUND TO THE INVENTION

The use of animals as models for the behaviour of materials administered to humans is well established. One area of such use is in the testing of vaccines. One class of vaccines which currently is available is the so-called conjugate vaccines, in which a strongly-immunogenic protein is coupled to weakly- or non-immunogenic bacterial polysaccharide, so as to elicit an immune response to the bacterial polysaccharide upon administration of the conjugate. One particular example is conjugation of diphtheria toxoid to the capsular polysaccharide of Haemophilus influenzae type b (PRP-D), as described in U.S. Pat. Nos. 4,496,538 and 4,619,828.

It has been observed when testing these conjugate vaccines in mice and subsequently testing the vaccines in infants, a much higher immune response was achieved in humans than predicted by the mouse testing. For the same immune response, PRP-D needed to be administered in mice at about 1/5th of the human infant dose level, whereas, if there was a true dose/weight relation, the mouse dose would be about 1/300 of the human infant dose level. In fact, we have observed that doses less than or equal to 1/25 of a human dose do not induce an immune response.

It has been demonstrated (ref. 1) that infants must be vaccinated with both diphtheria toxoid and PRP-CRM (a mutant diphtheria toxin) to induce an anti-PRP response. A similar effect has been observed in rhesus monkeys (ref. 2). These experiments indicated that the simultaneous or prior immunization with the carrier protein may affect the anti-PRP response induced by conjugate vaccines. These results may serve to explain the discrepancies observed above between mouse data and human data, since infants are typically vaccinated with a DTP combination (diphtheria-tetanus-pertussis) vaccine before or at the same time as they are vaccinated with PRP-conjugates. Mice tested with PRP-conjugate would not have been administered the DTP or D component, because there was considered no reason to do so.

SUMMARY OF INVENTION

Based on these observations, a new procedure for animal modelling of the immune response in humans to antigens has been formulated. In this regard, in accordance with the present invention, there is provided a method of testing the dose response of a human to a conjugate vaccine comprising a strongly-immunogenic carrier protein and a bacterial polysaccharide, which comprises administering to an animal unconjugated strongly-immunogenic carrier protein in an amount corresponding on a weight-scaled basis to a human dose thereof, simultaneously or subsequently administering to the animal a dose amount of said conjugated vaccine, and determining the immune response of the animal to the bacterial polysaccharide as a direct measure on a weight-related basis of the immune response of a human, to whom a human dose of the unconjugated strongly-immunogenic carrier protein has been previously or simultaneously administered, to the dosage amount of the conjugated vaccine.

GENERAL DESCRIPTION OF INVENTION

In the present invention, by modelling the condition of a human to whom a conjugate vaccine of a strongly-immunogenic carrier protein and a bacterial polysaccharide is to be administered, by simultaneously or pre-administering a weight-related dosage of unconjugated carrier protein, the anti-polysaccharide immune response of the animal to the conjugate gives an accurate prediction of the anti-polysaccharide immune response of a human to the conjugate.

The bacterial polysaccharide may be the capsular polysaccharide of Haemophilus influenzae type b (Hib) or other weakly- or non-immunogenic bacterial polysaccharide. Such bacterial polysaccharides include Streptococcus pneumoniae, Neisseria meningitidis, Salmonella typhi and Group B streptocci.

The highly-immunogenic carrier protein usually is diphtheria toxoid (DT) or mutation thereof, such as CRM197, but may be any other highly-immunogenic protein which is administered in unconjugated form, for example, the outer membrane protein (OMP) of Hib.

The carrier protein also may be tetanus toxoid. However, no difference in response to PRP-T conjugates is observed, both in animals and in humans, whether tetanus toxoid is coadministered with the conjugate or not. Other carrier proteins which may be used include OspA, cholera toxin, bacterial outer membrane proteins, other bacterial toxins, fungal proteins, parasitic proteins and vital proteins.

Animals used in the modelling procedure of the invention may comprise any of the animals normally employed to test vaccines, including mice, rats and guinea pigs. For mice, we found the best correlation to human infant primary and secondary immune responses to PRP-conjugates was achieved with co-administration of 1/50 of a human dose of PRP-D and PRP-CRM and 1/50 of a human dose of DT vaccine.

EXAMPLES

Example 1

Figure 1:
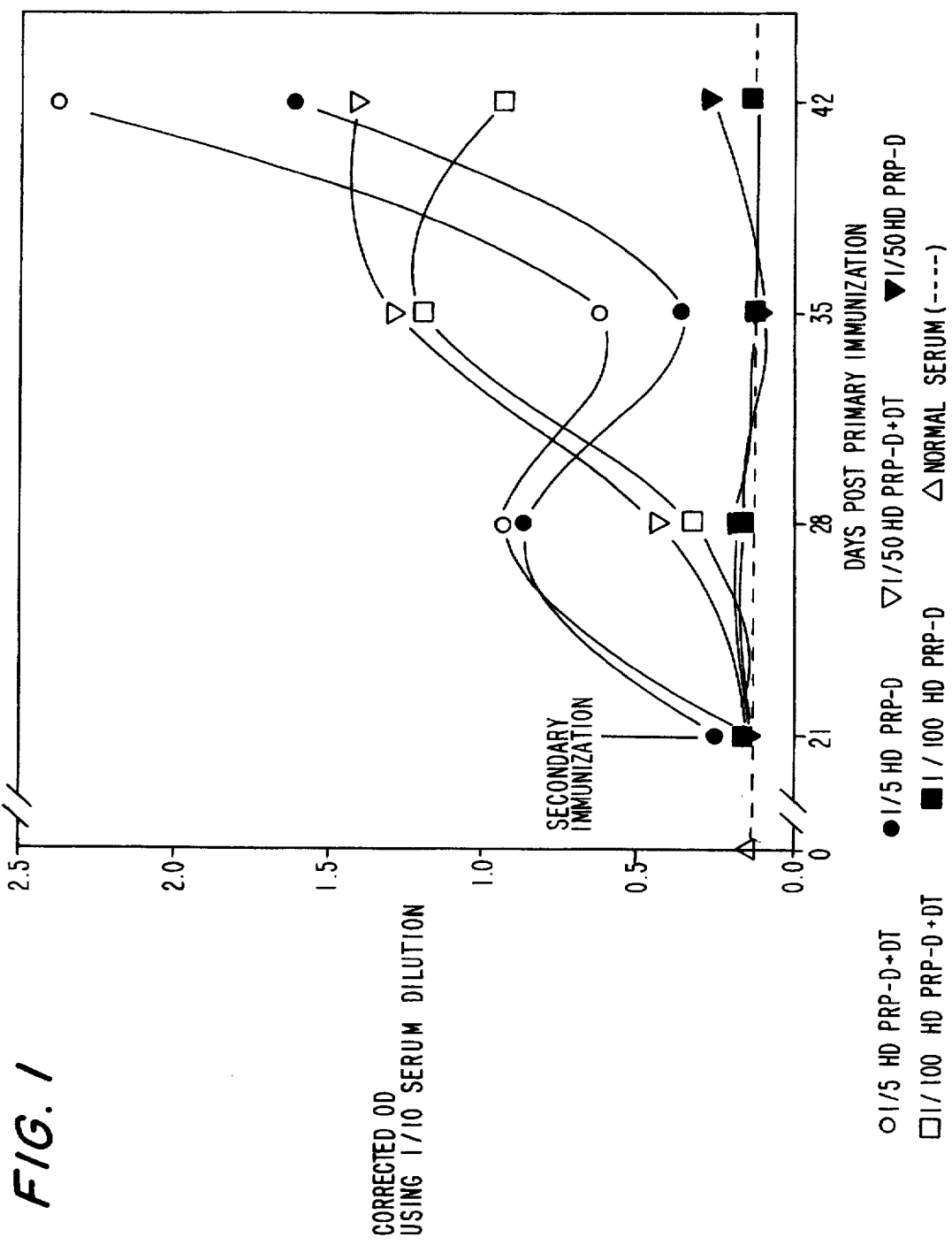
FIGS. 1 and 2 illustrate the time course of IgG responses to PRP-D in mice with and without coadministration of DT.
Figure 2:
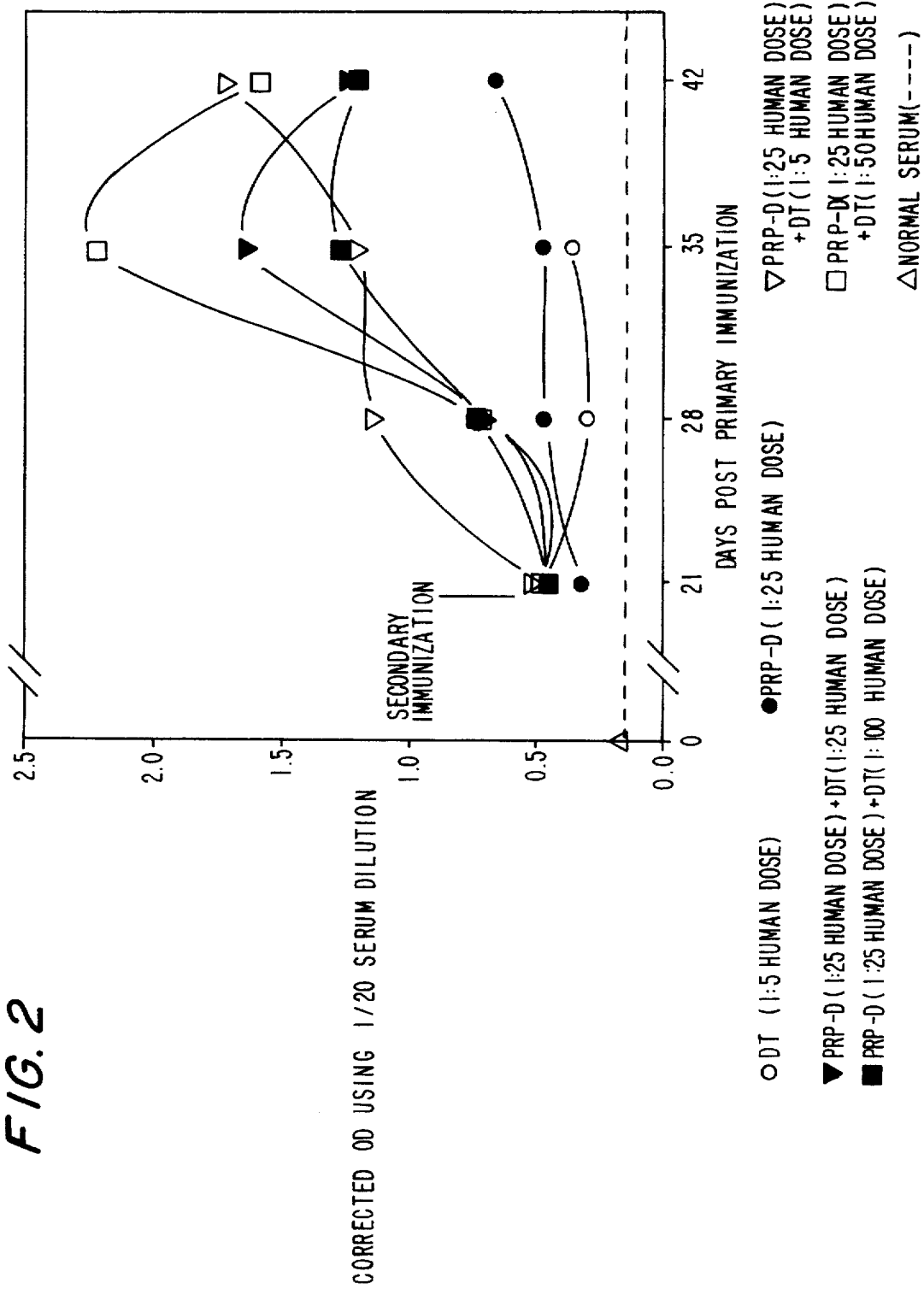

Mice were immunized with a conjugate of capsular polysaccharide from Hib and diphtheria toxoid at different proportions of the human dosage levels, with or without coadministration of DT vaccine (i.e. diphtheria and tetanus toxoid absorbed or alone) at a different site of injection from the conjugate, at different proportions of the human dosage. The results obtained are set forth in FIGS. 1 and 2.

As may be seen from this data, the mice did not respond to PRP-D at low doses (1/50 or 1/100 of a human dose) unless DT was first administered. Similarly, PRP-D did not induce a strong anti-diphtheria toxoid response unless coadministered with DT vaccine.

Example 2

Tests also were performed using pneumococcal carbohydrate 19F-diphtheria toxoid conjugate (19F-Dt). When administered alone, 19F-Dt vaccine induced an optimal response in mice at a dosage of approximately 5 µg/mouse, similar to the dose used for PRP-D alone. This dosage of 19F-Dt alone was compared to the coadministration of 1

µg/mouse of 19F-Dt with 1/50th a human dose of DT vaccine.

The results obtained after primary and secondary immunization were as set forth in the following Table:

| Antigen | Anti-19F Response | |
|---|---|---|
| | IgG | IgM |
| Saline | <18 | 9 |
| 19F-carbohydrate | <18 | 44 |
| 19F-Dt | 58 | 50 |
| 19F-Dt + DT | 1197 | 105 |

As may be seen, a considerable potentiation of anti-19F response was observed with coadministration of the DT.

SUMMARY OF DISCLOSURE

In summary of this disclosure, the present invention relates to an animal modelling procedure already an accurate dose-related response to bacterial polysaccharides can be achieved. Modifications are possible within the scope of this invention.

REFERENCES

1. Rathore et al, "Vaccination with Diphtheria-Tetanus Toxoids is Required for Infants to Respond at 2 & 4 Months of Age to HbOC conjugate but Not to *Haemophilus influenzae* type b 'Outer Membrane Protein (OMP)'", Abstract of the 1991 ICAAC, 110.
2. Vella et al, "Immunogenicity of *Haemophilus influenzae* type b Conjugate Vaccines in Infant Rhesus Monkeys" Pediatric Research, 29, 10–13.

What we claim is:

1. A method of testing the dose-related immune response of a human to conjugate vaccine comprising diphtheria toxoid and a capsular polysaccharide of *Haemophilus influenzae* type b of pneumococcal polysaccharide, which comprises:

administering to an animal unconjugated diphtheria toxoid in an amount corresponding on a weight-scaled basis to a human dose thereof, simultaneously administering to said animal a dose amount of said conjugate vaccine, subsequently administering to said animal a second dose amount of said conjugate vaccine; and determining the immune response of said animal to said capsular polysaccharide of *Haemophilus influenzae* type b or pneumococcal polysaccharide relative to the immune response of a human, to whom a human dose of said diphtheria toxoid has been previously administered, to said dose amount of said conjugate vaccine.

2. The method of claim 1, wherein said animal is a mouse.

* * * * *